(12) United States Patent
Kühner

(10) Patent No.: US 7,426,415 B2
(45) Date of Patent: Sep. 16, 2008

(54) NEUTRAL ELECTRODE FOR USE IN HF SURGERY

(75) Inventor: Ralf Kühner, Stuttgart (DE)

(73) Assignee: Erbe Elektromedizin GmbH, Tubingen (DE)

( * ) Notice: Subject to any disclaimer, the term of this patent is extended or adjusted under 35 U.S.C. 154(b) by 98 days.

(21) Appl. No.: 11/195,458

(22) Filed: Aug. 2, 2005

(65) Prior Publication Data

US 2005/0267456 A1    Dec. 1, 2005

Related U.S. Application Data

(63) Continuation of application No. PCT/EP2004/001024, filed on Feb. 4, 2004.

(30) Foreign Application Priority Data

Feb. 7, 2003    (DE) ............................... 103 05 125

(51) Int. Cl.
*A61N 1/06* (2006.01)
(52) U.S. Cl. ...................................... 607/152
(58) Field of Classification Search ................. 607/149, 607/152
See application file for complete search history.

(56) References Cited

U.S. PATENT DOCUMENTS

| | | | |
|---|---|---|---|
| 4,088,133 A | 5/1978 | Twentier | |
| 4,237,886 A | 12/1980 | Sakurada et al. | |
| 4,664,118 A * | 5/1987 | Batters | 607/46 |
| 4,873,974 A | 10/1989 | Hagen et al. | |
| 5,374,283 A | 12/1994 | Flick | |
| 6,453,203 B1 | 9/2002 | Yamazaki et al. | |
| 2004/0030270 A1 * | 2/2004 | Johnson | 601/15 |
| 2004/0254624 A1 * | 12/2004 | Johnson | 607/149 |
| 2006/0085047 A1 * | 4/2006 | Unsworth et al. | 607/48 |

FOREIGN PATENT DOCUMENTS

WO    99/60980 A2    12/1999

* cited by examiner

*Primary Examiner*—Carl H. Layno
*Assistant Examiner*—Yun Haeng Lee
(74) *Attorney, Agent, or Firm*—Dickstein Shapiro LLP

(57) ABSTRACT

In previously known neutral electrodes which are used in HF surgery, at least some portions comprise electrically conductive, stretchable, and flexible areas made of textile material, these areas being brought into contact with a body section of a patient. According to the invention, such an area is embodied as a stocking, tube, or similar anatomically shaped thromboembolism-preventing envelope, whereby secure contact of the neutral electrode is ensured without requiring any additional device.

10 Claims, 2 Drawing Sheets

NEUTRAL ELECTRODE FOR USE IN HF SURGERY

CROSS-REFERENCE TO RELATED APPLICATIONS

This application is a continuation of International Application No. PCT/EP2004/001024, filed Feb. 4, 2004, which was published in the German language on Aug. 19, 2004, under International Publication No. WO 2004/069070 A1 and the disclosure of which is incorporated herein by reference.

FIELD OF THE INVENTION

The present invention relates to a neutral electrode for use in HF (High Frequency) surgery.

BACKGROUND OF THE INVENTION

Adhesive electrodes (for single use) are known that require the surface to which they are to be attached to be shaved before application of the electrode, in order to ensure secure contact and adhesion. This is not optimal, for hygienic and aesthetic reasons. It can also result in skin irritations or allergic reactions, because a conductive (adhesive) gel is used.

Furthermore, neutral electrodes with a purely capacitive action are known, which are installed by laying them on the operating table. However, because this layer can only be disinfected and not sterilized, in addition a special sterile covering must be used for each operation to satisfy the hygienic requirements. Therefore such neutral electrodes are very expensive.

German Patent DE PS 564819 discloses a neutral electrode, which in its main sections comprises an electrically conductive, stretchable and flexible surface of textile material that can be brought into contact with part of a patient's body by fixing the electrode in place by means of a belt-like arrangement put onto the patient. This known neutral electrode, however, often presents problems with respect to making correct contact, and also places additional stress on the patient when it is firmly attached because vascular constriction can occur.

BRIEF SUMMARY OF THE INVENTION

It is the object of the invention to provide a neutral electrode for use in HF surgery that provides an electrical contact by simple means that is both advantageous for the patient and electrically reliable.

According to the present invention there is provided a neutral electrode for use in HF surgery comprising a stretchable and flexible anatomically shaped thromboembolism-preventing envelope made of a textile material that at least regionally (locally) is electrically conductive and that can be brought into contact with part of a patient's body.

It is the aim of the invention that with this neutral electrode, so to speak, "two flies are struck with one blow". On one hand, in extremely many operations thromboembolism-preventing envelopes are used, in particular stockings, and now this stocking (which is in contact with the patient in any case) simultaneously forms the neutral electrode. Another surprising advantage lies in the fact that application of the neutral electrode, which is problematic in the case of the object disclosed in the above-mentioned German Patent DE PS 564819, now occurs "inevitably" in the correct way, with a firm seating, because precisely this property is associated with the action of thromboembolism-preventing envelopes or stockings.

Preferably at least two surface sections that are electrically insulated from one another are provided, so that by means of measuring devices (known per se) it can be determined whether the neutral electrode is making correct contact with the skin.

Preferably the textile material incorporates threads, strips or ribbons of conductive material, which are woven or knitted into the textile or are inserted as an internal layer, so that manufacture can be very easily accomplished. In this case the conductive material is preferably introduced in such a way (e.g., folded or puckered) that the textile structures become maximally extended before any tension is applied to the conductive material. Hence if (over-) stretching occurs, the textile material tears before the conductive material alters its properties.

The electrical connection devices joined to the electrically conductive sections are preferably disposed on an external surface of the envelope in such a way that the electrical supply leads can be freely coupled thereto. As a result it is possible to attach the supply leads without getting in the way of the operating-room personnel.

The connection devices here preferably comprise a rotary joint such that when coupled thereto, the supply leads can be rotated substantially freely about the connection devices. This makes it possible to dispose the supply leads in places where they do not interfere with the operation. In particular, this is possible when the connection devices comprise a pushbutton or similar releasable connection, so that if two (or more) electrically conductive surfaces are provided, the connection devices comprise a coaxial contact or similar multiple contact for connecting several electrically conductive sections to a multicontact supply lead. The result is not only an especially simple, time-saving and secure contact, but it is also especially simple to position the connection device so that it is out of the way.

The electrically conductive sections are preferably inhomogeneously distributed over the area, to adapt them to the electrical properties of the part of the body to which they are applied. This measure deals with the problem that an excessively high current density in joint regions such as the knee or elbow might cause undesired tissue damage.

It is particularly preferred, when the textile area is constructed as a stocking, for the connection devices to be situated at a toe-tip of the stocking. As a result, there is practically no kind of patient positioning that would produce pressure points, at which the connection device is pressed into the tissue.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
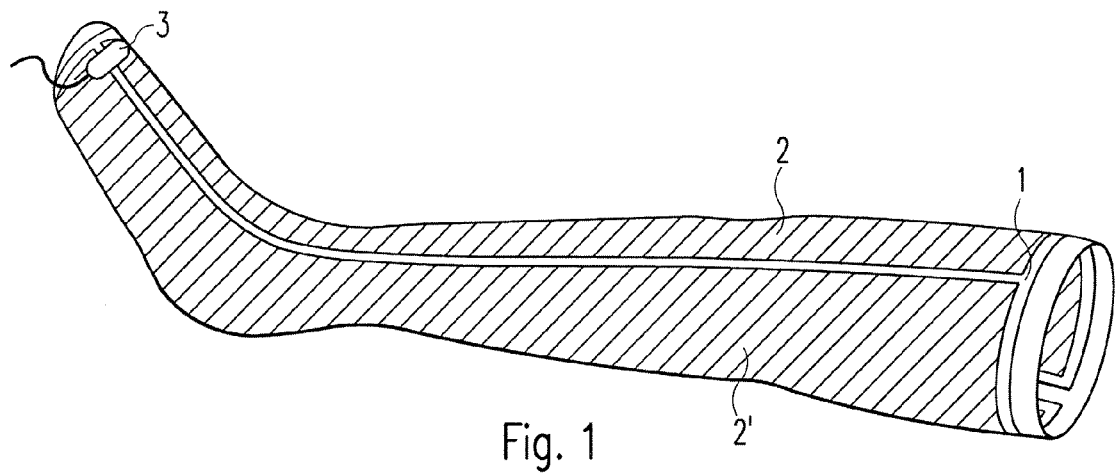
FIG. 1 is a perspective illustration of a first embodiment of the invention.

In the following description, the same reference numerals are used for identical parts or parts with identical actions.

In the exemplary embodiments illustrated here, a stocking-shaped thromboembolism-preventing envelope is shown. However, it should be pointed out that envelopes can also be produced that conform to other parts of the body, for instance those that can be fitted to the arms or also to the hands in the form of gloves.

The embodiment shown in FIG. 1 is a stocking that incorporates elastic strands, which endow the textile with the compressive thromboembolism-preventing property in both the longitudinal and the transverse directions ("double-stretch" stocking). The fabric 1 is provided in two regions 2, 2' with electrically conductive structures, which can take the form of thin metallic strands or other thin, non-metallic conductive structures (e.g., carbon fibers). These strands or structures can be woven or knitted together with the stocking or area 1. The conductive strands can be disposed in such a way that they make direct contact with the skin surface and hence have an exclusively conductive action. In another embodiment of the invention the strands are provided with an insulating layer (e.g., a thin covering of silicone) so as to prevent direct contact with the skin. As a result, purely capacitive electrical connections are created. Such capacitive electrodes can also be produced by adding the conductive structure as a middle (or outer) layer of the fabric-like structure. In particular when the fabric is manufactured as knitted or woven goods, the proportion of areas with conductive and capacitive actions can be nearly arbitrarily selected or even combined to suit the requirements, which was not possible with the previously customary electrodes. The conductive areas 2, 2' of the neutral electrode can also be attached by printing techniques, preferably by screen-printing and/or vapor deposition and/or spraying on a conductive layer. Combinations of the various forms of manufacture are also easily possible here.

The conductive sections 2, 2' of the neutral electrode according to FIG. 1 are provided in the toe region of the stocking with electrical connection devices 3. By way of these electrical connection devices the electrically conductive sections 2, 2' are connected to an electrosurgical apparatus in a manner known per se.

Figure 3:
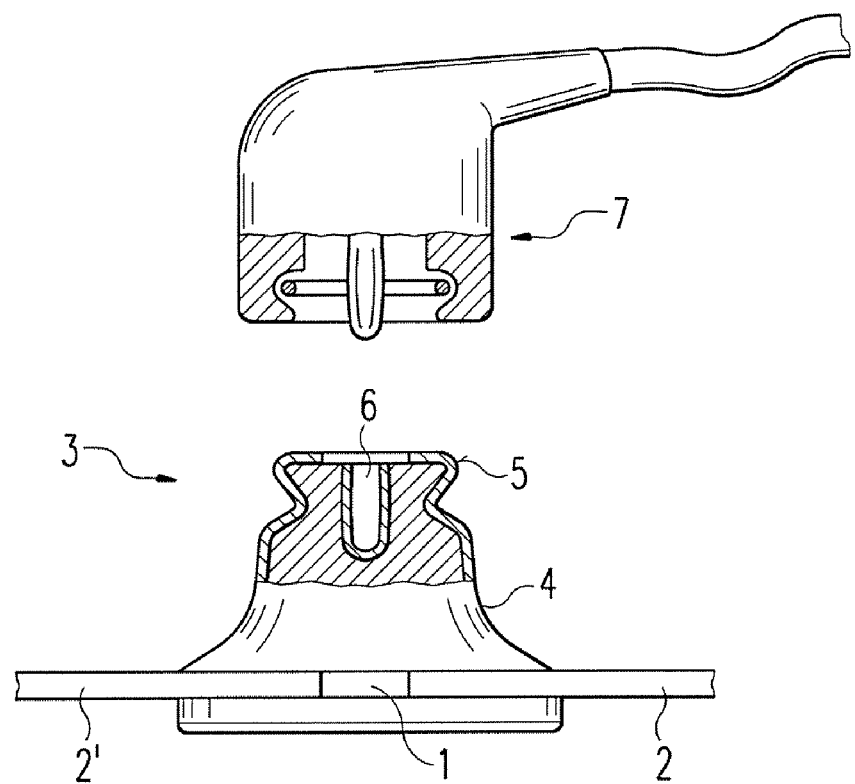
FIG. 3 is a partially sectioned illustration of a connection device.

An embodiment of the connection device 3 is shown in FIG. 3. It comprises a pedestal part 4, which incorporates an outer, conductive contact area 5 in the form of a push-button and, coaxial with this area, an internal socket 6. There are electrically conducting connections between the outer contact area 5 and the section 2, and between the socket 6 and the other section 2'. A correspondingly shaped plug 7 completes the connection device 3 in such a way that the plug contact 7 can be rotated about the pedestal part 4 while maintaining the electrical contact. With a connection device 3 thus disposed and constructed, the orientation of the neutral-electrode cable leaving the operating table can be nearly freely selected to suit the patient's position, because the cable outlet can be freely rotated about the connection device 3. It is of course also possible to provide two separate connection devices (which in turn can be constructed as push-buttons).

Figure 2:
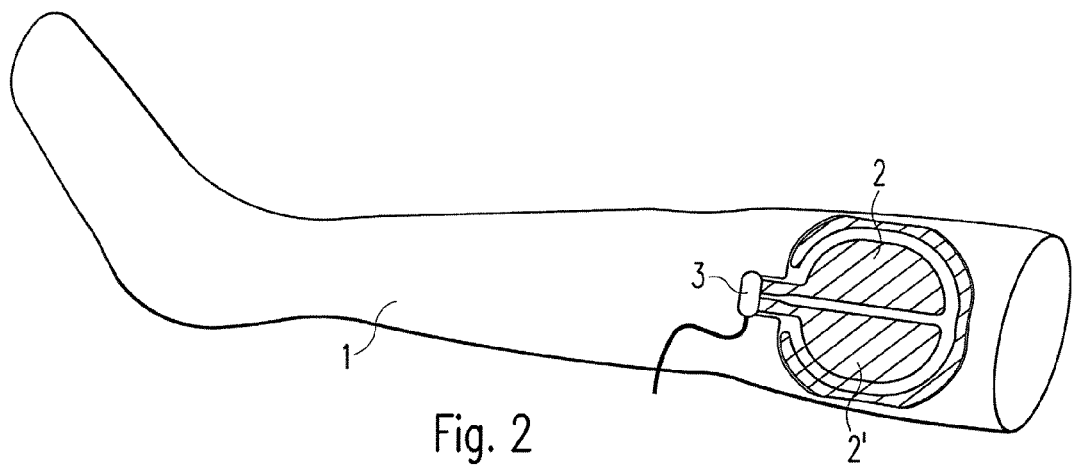
FIG. 2 is a perspective illustration of a second embodiment of the invention.

In the embodiment of the invention shown in FIG. 2, the stocking 1 contains in its thigh region two sections 2, 2' provided with electrically conductive structures, so that the neutral electrode is restricted to this region. The electrical connection devices 3 are also disposed in this region. However, it is also possible, by way of electrically insulated supply leads that are preferably woven or knitted into the fabric, to connect the electrically conducting sections 2, 2' to an electrical connection device 3 disposed at the toe of the stocking 1.

I claim:

1. A neutral electrode comprising a stretchable and flexible anatomically shaped thromboembolism-preventing envelope made of a textile material with compressive thromboembolism preventing property that is at least regionally electrically conductive and that can be brought into contact with a part of a patient's body, the neutral electrode forming part of a high frequency surgery system and configured to avoid high current density of a high frequency current introduced into biological tissue from a high frequency surgical instrument.

2. The neutral electrode according to claim 1, wherein at least two electrically conductive regions that are electrically insulated from one another are provided in the envelope with separate electrical connection devices.

3. The neutral electrode according to claim 2, wherein the envelope is constructed as a stocking and connection devices are disposed at a toe-tip of the stocking.

4. The neutral electrode according to claim 1, wherein the textile material comprises at least one of strands, strips and ribbons which are made of electrically conductive material, and which have been incorporated into the material by one of the following techniques: weaving; knitting; printing; spraying on; and insertion as a internal layer.

5. The neutral electrode according to claim 1, wherein electrical connection devices are connected to the electrically conductive regions disposed on an outer surface of the envelope in such a way that supply leads can be freely coupled to the connection devices.

6. The neutral electrode according to claim 5, wherein the connection devices comprise a rotary joint, so that supply leads coupled to the rotary joint are freely rotatable about the connection devices.

7. The neutral electrode according to claim 6, wherein the connection devices comprise a push-button releasable connection.

8. The neutral electrode according to claim 5, wherein the connection devices comprise a coaxial contact for the connection of a plurality of electrically conductive sections to a multicontact supply lead.

9. The neutral electrode according to claim 1, wherein the electrically conductive material is distributed non-homogeneously over a surface of the envelope, so as to be adapted to electrical properties of the body part to be contacted.

10. The neutral electrode according to claim 1, wherein the textile material comprises elastic strands that endow the textile material with a compressive thromboembolism-preventing property.

* * * * *